United States Patent [19]

Bredehorst et al.

[11] Patent Number: 5,106,762
[45] Date of Patent: Apr. 21, 1992

[54] LIGAND-LABEL CONJUGATES WHICH CONTAIN POLYOXOANIONS OF SULFUR OR PHOSPHORUS

[75] Inventors: Reinhard Bredehorst, Washington, D.C.; Frances S. Ligler, Potomac, Md.; Anne W. Kusterbeck, Falls Church; Gregory A. Wemhoff, Manassas, both of Va.; Carl-Wilhelm Vogel, Washington, D.C.

[73] Assignee: Georgetown University, Washington, D.C.

[21] Appl. No.: 512,272

[22] Filed: Apr. 20, 1990

[51] Int. Cl.⁵ ............... G01N 33/532; G01N 33/533; C07K 7/40
[52] U.S. Cl. .................. 436/546; 436/501; 436/543; 436/544; 436/547; 530/303; 530/324; 530/325; 530/326; 530/327; 530/328; 530/329; 530/330
[58] Field of Search ............. 530/303, 324, 325, 326, 530/327, 328, 329, 330, 345; 4335/964, 968, 7.92, 7.93, 7.94; 436/543, 544, 546, 547, 800, 819, 822, 823

[56] References Cited

U.S. PATENT DOCUMENTS

| | | | |
|---|---|---|---|
| 4,014,861 | 3/1977 | Geiger et al. | 530/303 |
| 4,166,105 | 8/1979 | Hirschfeld | 436/536 |
| 4,430,266 | 2/1984 | Frank | 530/303 |
| 4,604,364 | 8/1986 | Kosak | 436/501 |
| 4,610,868 | 9/1986 | Fountain et al. | 435/1 |
| 4,645,646 | 2/1987 | Gadow et al. | 436/531 |

OTHER PUBLICATIONS

M. Tal et al., Chem. Abst., vol. 103, No. 156719x (1985).

Primary Examiner—Mary E. Ceperley
Attorney, Agent, or Firm—Oblon, Spivak, McClelland, Maier & Neustadt

[57] ABSTRACT

Ligand-label conjugates which are an oligopeptide of 5 to 100 amino acid residues, bonded to a ligand or receptor, which contain a plurality of chemiluminescent or fluorescent labels and a plurality of polyoxoanions of sulfur or phosphorus are useful for immunoassays. Such conjugates are hydrophilic and exhibit very low non-specific binding, thereby significantly increasing the signal to background ratio in immunoassays.

46 Claims, 3 Drawing Sheets

LIGAND-LABEL CONJUGATES WHICH CONTAIN POLYOXOANIONS OF SULFUR OR PHOSPHORUS

BACKGROUND OF THE INVENTION

1. Field of the Invention

The present invention relates to novel fluorescent-labeled or chemiluminescent-labeled conjugates for use in specific binding assays for ligands (e.g., antigens and haptens) or receptors (e.g., antibodies, specific binding proteins, and cell surface receptors). The invention further relates to intermediate compounds produced in the synthesis of the novel labeled conjugates, and kits containing such labeled conjugates and/or intermediates.

2. Discussion of the Background

Presently, several immunochemical methods exist for the detection of ligands such as haptens, antigens or antibodies. Radioimmunoassay is a widely used method. This method employs a radioisotope-labeled antigen (ligand) to compete with the antigen from a test sample for binding to a specific antibody. U.S. Pat. No. 3,709,868 describes such a radioimmunoassay. While by definition, radioimmunoassay is based on the binding of a specific antibody with an antigen or hapten, radioactive binding assays which are based on other specific binding interactions, such as between hormones and their binding proteins, have also been developed.

Several non-isotopic immunoassays have been proposed to eliminate the disadvantages associated with radioactive materials. Ligands such as an antigen or hapten and receptors such as an antibody have been labeled with a variety of non-radioactive compounds, including chemiluminescent and fluorescent molecules.

Specific examples of useful chemiluminescent labels are disclosed in German OLS No. 2,618,511 and include luminol (3-aminophthalhydrazide or 5-amino-2,3-dihydro-1,4-phthalazinedione) and isoluminol (4-aminophthalhydrazide or 6-amino-2,3-dihydro-1,4-phthalazinedione). The use of N-(4-aminobutyl)-N-ethylisoluminol (6-[N-(4-aminobutyl)-N-ethylamino]-2,3-dihydrophthalazine-1,4-dione) as a chemiluminescent label is reported in Simpson et al., Nature, Vol. 279, p. 646 (1979). The preparation of chemiluminescent phthalhydrazide labeled ligands is described in U.S. patent application Ser. No. 927,621, filed July 24, 1978, entitled "Chemiluminescent Phthalhydrazide Labelled Conjugates." U.S. Pat. No. 4,331,808 discloses labeling ligands with chemiluminescent naphthalene-1,2-dicarboxylic acid hydrazide using straight chain alkyl groups as spacers between the label and the ligand.

While these chemiluminescent compounds have been shown to be suitable labels, they are hydrophobic and, thereby, increase the hydrophobicity of the ligand complex. For example, column chromatographic purification of synthesized thyroxin-naphthalene-1,2-dicarboxylic acid hydrazide conjugates requires the use of organic solvents (U.S. Pat. No. 4,331,808). A documented disadvantage of an increased hydrophobicity is an increase in nonspecific binding effects. This results in a decreased signal to background ratio of immunoassays.

U.S. Pat. No. 4,645,646 describes the use of hydrophilic chain-like polymers with recurring functional groups (e.g., proteins) as carriers of multiple chemiluminescent luminol molecules to improve the sensitivity of luminescence immunoassays. However, these conjugates exhibit non-specific binding properties. In fact, some of the disclosed conjugates exhibit such marked non-specific binding properties to preclude their use in immunoassays (U.S. Pat. No. 4,645,646). These examples demonstrate that currently available techniques for coupling chemiluminescent labels to ligands pose an inherent problem. The hydrophobic properties of the chemiluminescent labels decrease the water solubility of the ligands to an extent that the sensitivity of the immunoassay is significantly reduced due to high non-specific background binding.

Labeling of ligands with fluorescent molecules poses very similar problems. Evrain et al., Steroids, vol. 35, 611-619 (1980) describe the synthesis of three fluorescein-labeled derivatives of testosterone using either cysteamine, or 1,3-diaminopropane, or 1,7-diaminoheptane as spacer between the fluorophore and the ligand. All derivatives proved to be highly hydrophobic. For example, analysis of the testosterone fluorescein conjugates by thin-layer chromatography on silica gel required the use of a combination of benzene:ethyl acetate:acetone (1:8:1) or chloroform:ethanol (7:3) as the solvent system. The hydrophobic nature of this compound is typical of fluorescein-labeled molecules and generally leads to high background readings in immunoassays.

U.S. Pat. No. 4,670,406 describes the use of bifunctional aromatic compounds (e.g., paranitrophenylisocyanate) as rigid coupling compounds for the synthesis of labeled ligands such as fluorescein-labeled digoxin. These rigid coupling reagents are advantageous in that they do not permit the fluorescent marker to "fold back" onto the ligand, thereby minimizing the possibility of quenching of the fluorescent compound by the ligand. However, as a result of their hydrophobic properties, the rigid coupling reagents further contribute to the loss of the water-solubility of the ligands upon labeling with fluorophores.

U.S. Pat. No. 4,452,886 describes the synthesis of ligand-containing polymers as carriers of multiple photon emitting (fluorescent) compounds. The disclosed polymers include proteins and synthetic or natural polypeptides having a large number of diamino acids for covalent attachment of photon emitting compounds or polymers of such compounds. Similar approaches have also been described in other publications. U.S. Pat. No. 4,604,364 discloses tracer compositions for immunoassays which contain photon emitting compounds coupled to ligands via an intermediate support material such as a protein or polypeptide. U.S. Pat. Nos. 4,166,105 and 4,169,137 describe antigen detecting reagents which are prepared by covalently linking fluorescent dye molecules to an appropriate antibody through a polymeric backbone having reactive functional groups along the length of its chain. Polymer backbone molecules reported to be suitable are polyethyleneimines (molecular weight range 1200 to 60,000 daltons), polypeptides such as polylysines, polyamides such as nylon-6, and low molecular weight (100 to 10,000 daltons) polymeric carboxylic acids. While such polymers help to reduce the loss of antibody binding activity upon fluorescent labeling, they are not suitable to compensate sufficiently for the hydrophobic properties of fluorescent labels such as fluorescein. As a result, such antigen detecting reagents exhibit significant non-specific background binding, thereby limiting the signal to background ratio of immunoassays. This is clearly demonstrated by a recent observation, in which antibody molecules labeled with only three fluorescein residues per antibody exhibited an approximately tenfold higher non-specific binding than the same antibodies labeled with iodine-125 (personal communication, Lisa Shriver-Lake (1990)).

| Specific and Non-specific Binding for DTAF- and $^{125}$I-Labeled Goat IgG (Shriver-Lake (1990)). | | | |
|---|---|---|---|
| Labeled Antigen | Amount of Labeled Antigen Bound to Immobilized anti-Goat IgG (Specific Binding) | Amount of Labeled Antigen Bound to Immobilized Non-immune IgG (Nonspecific Binding) | Ratio of Specific to Nonspecific Binding |
| $^{125}$I-labeled Goat IgG | 447.9 ng | 30.4 ng | 14.73 |
| DTAF-labeled Goat IgG (3.1 DTAF/IgG) | 12.97 FU | 9.52 FU | 1.36 |

FU: arbitrary fluorescence units; DTAF: 5-(4,6-dichlorotriazinyl)aminofluorescein. The specific and nonspecific binding ratios for the DTAF-labeled goat IgG and the $^{125}$I-labeled goat IgG were measured using affinity purified anti-goat IgG (Jackson ImmunoResearch, West Grove, PA) covalently attached to cover slips by N-γ-maleimidobutyryloxy succinimide ester (GMBS) as described in Bhatia et al, Anal. Biochem., vol. 178, pp. 408–413 (1989).

Thus, even a highly hydrophilic polypeptide chain such as an antibody with a molecular weight of approximately 150,000 apparently cannot compensate for the hydrophobic properties of as few as three fluorophore molecules.

Accordingly, there remains a need for molecular carriers which can link fluorescent or chemiluminescent labels to ligands, such as antigens and haptens, or receptors, such as antibodies, specific binding proteins and cell surface receptors, which do not suffer from the above-mentioned drawbacks. In particular, there remains a need for fluorescent-labeled and chemiluminescent-labeled conjugates which possess good water solubility, and for compounds which contain a plurality of fluorescent or chemiluminescent labels or sites for attaching such labels and which may be conveniently covalently bonded to a ligand, such as an antigen, hapten, or a receptor, such as an antibody, etc., to provide a ligand-label conjugate with good water solubility.

SUMMARY OF THE INVENTION

Accordingly, it is an object of the present invention to provide novel conjugates in which chemiluminescent or fluorescent labels are linked to ligands or receptors.

It is another object of the present invention to provide novel conjugates, in which chemiluminescent or fluorescent labels are linked to ligands and receptors, which are hydrophilic.

It is another object of the present invention to provide novel conjugates, in which chemiluminescent or fluorescent labels are linked to ligands and receptors, in which the quenching of the label by the ligand is minimized.

It is another object of the present invention to provide diagnostic kits which contain such conjugates of ligands or receptors and fluorescent or chemiluminescent labels.

It is another object of the present invention to provide novel labeled compounds in which a plurality of fluorescent or chemiluminescent labels are bonded to a linker which possesses a unique functional group for bonding a ligand or a receptor.

It is another object of the present invention to provide novel ligand compounds in which a ligand or a receptor is bonded to a linker molecule which possesses a plurality of functional groups for bonding a plurality of fluorescent or chemiluminescent labels.

These and other objects, which will become apparent during the course of the following detailed description have been achieved by ligand-label conjugates in which an oligopeptide is bonded to a ligand or receptor, and in which at least one of the amino acid residues contains a polyoxoanion group of sulfur or phosphorus and a plurality of the amino acid residues are linked to a chemiluminescent or fluorescent label; the intermediate compounds for coupling the ligand and/or labels to such conjugates; and kits containing such conjugates.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

Figure 1:
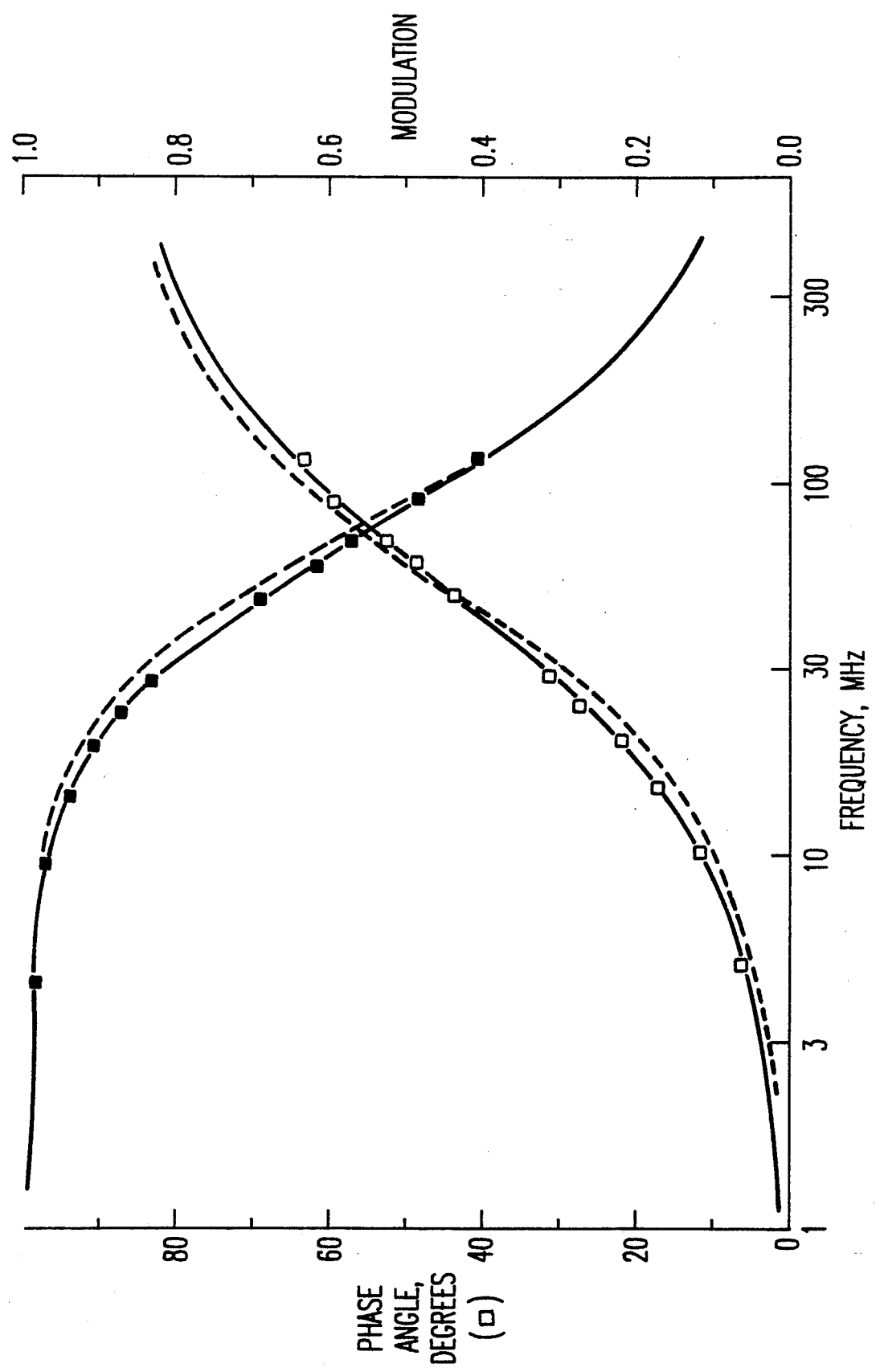
FIG. 1 illustrates the fluorescence lifetime of the DNP-insulin A-chain-fluorescein conjugate. Shown are the frequency-dependent phase (□) and modulation ( ) data, together with the best one (— — —) and two (———) component fits. The precision of the data is approximately ten-fold better (phase: 0.2 degrees; modulation: 0.002) than suggested by the size of the data points.

In one aspect, the present invention relates to conjugates in which a natural or synthetic polypeptide oligomer is bonded to a ligand or receptor, and in which at least one of the amino acid residues contains a polyoxoanion of sulfur or phosphorus and a plurality of the amino acid residues are linked to a chemiluminescent or fluorescent label. The polypeptide backbone of the molecule may suitably contain 5 to 100 amino acid residues, preferably 10 to 50 amino acid residues, most preferably 15 to 25 amino acid residues.

The present conjugates may thus be represented by the general formula (I):

$$(aa_1)(aa_2)(aa_3)\ldots(aa_n) \qquad (I)$$

wherein n is an integer of from 5 to 100, preferably 10 to 50, most preferably 15 to 30, and $(aa_1)\ldots(aa_n)$ represent amino acid residues, and wherein at least one of the amino acid residues contains a polyoxoanion of sulfur or phosphorus, a plurality of the amino acid residues are linked to a fluorescent or chemiluminescent label, and one of the amino acid residues is bonded to a receptor or ligand.

The present conjugates are easily prepared from synthetic or natural polypeptide oligomers which contain three types of functional groups: (i) a unique first functional group for bonding a ligand or receptor; (ii) at least one of a second functional group which may be derivatized to contain a polyoxoanion of phosphorus or sulfur; and (iii) a plurality of a third functional group which can be linked to a chemiluminescent or fluorescent label. Alternatively, the starting oligopeptide may be one which already contains at least one polyoxoanion, such as insulin A-chain in the tetra-S-sulfonate form and thus, is not required to possess the second type of functional group described above.

The unique functional group for bonding the ligand is preferably located at one end of the polypeptide oligomer chain. Accordingly, it is preferred that this functional group be either a $NH_2-$ group or a $-CO_2H$ group, since these reactive groups are the natural terminators of polypeptide chains.

In this case, the conjugate may have either formula (II) or (III):

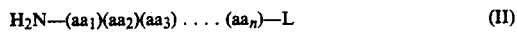  (II)

  (III)

in which the definitions of formula (I) apply and L is a ligand or receptor.

It is particularly important that the functional group for bonding the ligand be a unique group and that only one ligand is attached to the polypeptide backbone. This is of particular importance for the detection of small molecular weight ligands in competitive immunoassays. Since the signal in such assays is usually generated by the release of labeled ligand from the antibody, increased sensitivity is achieved if the ligand is bound by only one antibody binding (Fab') site. If two or more ligands were included in the labeled conjugate, one ligand could be displaced while another remained bound to, for example, an antibody-coated solid support.

The term ligand, as used herein, refers to a molecule such as an antigen or hapten which binds to a corresponding receptor such as an antibody. Generally, such ligands include, for example, drugs, hormones, proteins, vitamins, and infectious agents. The term receptor, as used herein, includes, for example, antibodies, specific binding proteins, and cell surface receptors. As discussed above, the present conjugates containing ligands and receptors are useful reagents for quantitative and qualitative measurements of the same ligand or receptor in homogeneous and heterogeneous immunoassay systems.

Representative of receptors are antibodies in general, particularly those of the IgG, IgE, IgM and IgA classes, for example hepatitis B antibodies; and representataive of ligands are antigenic proteins such as insulin, chorionic gonadotropin (e.g., HCG), carcinoembryonic antigen (CEA), myoglobin, hemoglobin, follicle stimulating hormone, human growth hormone, thyroid stimulating hormone (TSH), human placental lactogen, thyroxine binding globulin (TBG), intrinsic factor, transcobalamin, enzymes such as alkaline phosphatase and lactic dehydrogenase, hepatitis-associated antigens such as hepatitis B surface antigen ($HB_sAg$), hepatitis e antigen ($HB_eAg$) and hepatitis core antigen ($HB_cAg$) and any antigens derived from HIV such as, e.g., gp120. Representative of polypeptide ligands are angiotensin I and II, C-peptide, oxytocin, vasopressin, neurophysin, gastrin, secretin, and glucagon.

Since, as peptides, ligands of this general category comprise numerous available carboxylic acid and amino groups, coupling to either the terminal $-NH_2$ or $-CO_2H$ group of the oligopeptide backbone can proceed according to conventional peptide condensation reactions such the carbodiimide reaction, the mixed anhydride reaction, and so forth, or by the use of conventional bifunctional reagents capable of coupling carboxylic acid or amino functions to either the terminal $-NH_2$ or $-CO_2H$ group of the oligopeptide backbone. General referencs concerning the coupling of proteins to primary amines or carboxylic acids include Science, vol. 144, p. 1344 (1964); Erlanger et al., Meth. in Immunology and Immunochemistry, Williams and Chase, eds, Academic, New York, p. 149 (1967); Kopple, Peptides and Amino Acids, Benjamin, New York (1966); Clin. Chem., vol. 22, p. 726 (1976); Immunochem., vol. 6, p. 53 (1969) and Lowe et al, Affinity Chromatography, Wiley, New York (1974).

Hapten ligands which themselves contain carboxylic acid functions, and which thereby can be coupled directly to the terminal $-NH_2$ group of the oligopeptide backbone, include the iodothyronine hormones such as thyroxine and liothyronine, as well as other materials such as biotin, valproic acid, folic acid and certain prostaglandins. Representative synthetic routes for preparing carboxylic acid binding analogs of hapten ligands which themselves do not contain an available carboxylic acid function, whereby such analogs can be coupled to the terminal $-NH_2$ group of the oligopeptide backbone by the aforementioned peptide condensation reactions or bifunctional coupling agent reactions, are given in U.S. Pat. No. 4,331,808, which is incorporated herein by reference. Thus, haptens such as carbamazepine, quinidine, digoxin, digitoxin, theophylline, phenobarbital, primidone, diphenylhydantoin, morphine, nicotine, androgens, estrogens, and progesterones may be bonded to the terminal $NH_2$ group of the oligopeptide backbone. Compounds such as cocaine may also be linked to the terminal $-NH_2$ group of the oligopeptide backbone. In addition, compounds which possess leaving groups may also be bonded to the terminal $NH_2$ group. For example, the trinitrophenyl or dinitrophenyl group may be attached by the reaction of fluorotrinitrobenzene or fluorodinitrobenzene with the terminal $NH_2$ group of the oligopeptide.

As noted above, the ligand or receptor may be bonded to the oligopeptide backbone via a conventional bifunctional spacer. The binding of a low molecular weight hapten, such as, e.g., the trinitrophenyl group, to the oligopeptide via a spacer can be advantageous in that the accessibility of the hapten for binding with its complement (antibody) may be increased A suitable spacer is, e.g., $-(CH_2)_m-S-S-$ (wherein m is 2 to 10, preferably 4 to 6). For example, the dinitrophenyl group may be bonded to the terminal $-NH_2$ group of the oligopeptide as shown below.

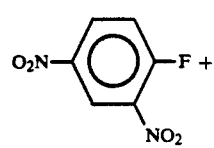

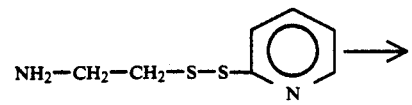

-continued

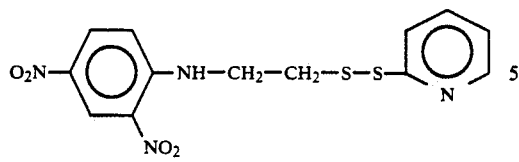

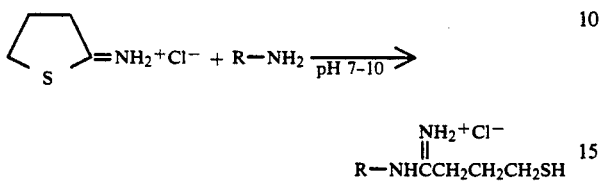

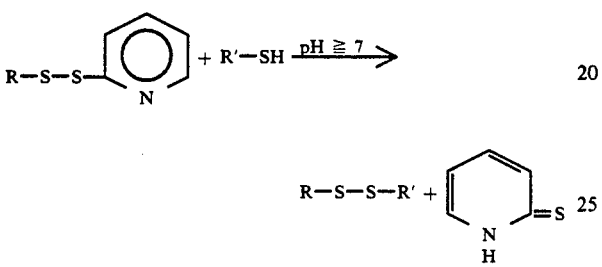

In the first step S-(2-thiopyridyl)-cysteamine prepared by the reaction of 2,2'-dithiopyridine with cysteamine in methanol (Chong et al, *J. Biol. Chem.*, Vol. 256, pp. 5064-5070 (1981)), is reacted with dinitrofluorobenzene. At the same time, the terminal —$NH_2$ group of the oligopeptide backbone is derivatized with Traut's reagent (2-iminothiolane) (Jue et al, *Biochemistry*, Vol. 17, pp. 5399-5406 (1978)). Then, the derivatized oligopeptide is coupled via the free sulfhydryl group to the pyridyldithio group of the derivatized hapten.

Other, bifunctional linkers which may be used to introdue spacers between the ligand or receptor and the oligopeptide backbone include those described in Haugland, *Handbook of Fluorescent Probes and Research Chemicals*, Molecular Probes, Inc., Eugene, Oregon (1989) and *Pierce Immunotechnology Catalog and Handbook*, Pierce, Rockford, Il (1990), e.g., succinimidyl trans-4-(N-maleimidylmethyl)-cyclohexane-1-carboxylate; succinimidyl 4-(p-maleimidylphenyl)butyrate; succinimidyl 6-((iodoacetyl)amino)hexanoate; succinimidyl 6-(6(((iodoacetyl)amino)hexanoyl)amino)hexanoate; succinimidyl 3-(2-pyridyldithio)propionate; and N-succinimidyl S-acetylthioacetate.

Thus, the oligopeptide and the ligand or receptor may be reacted with one of the above-mentioned molecules to introduce one of the following terminal functional groups:
polypeptide-SH
polypeptide-S-S-2-pyridyl polypeptide-$\overset{O}{\overset{\|}{C}}CH_2I$ polypeptide-maleimidyl
ligand-SH
ligand-S-S-2-pyridyl ligand-$\overset{O}{\overset{\|}{C}}CH_2I$ ligand-maleimidyl
The derivatized ligand or receptor may then be coupled with the derivatized oligopeptide as shown in the scheme below:

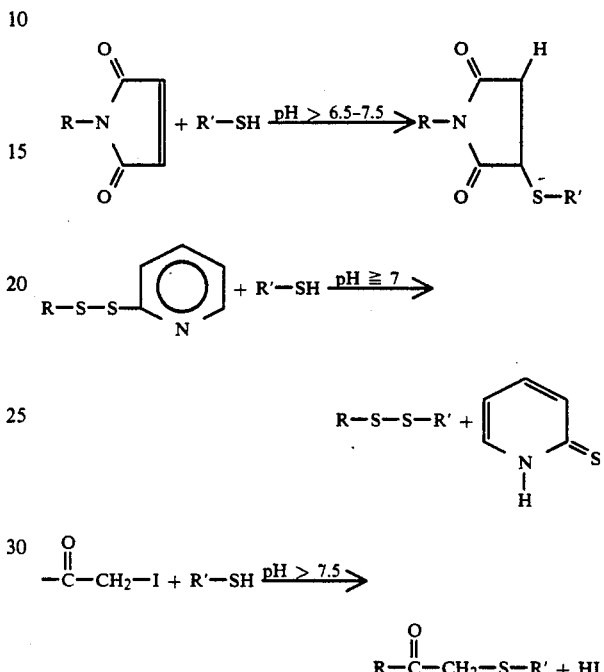

Alternatively, either the ligand or oligopeptide can be derivatized with N-succimidyl S-acetylthioacetate resulting in a terminal S-acetyl group which can be deprotected with neutral $NH_2OH$ to yield a free sulfhydryl group which can be coupled as shown above.

Thus, the ligand may be conveniently linked to the oliopeptide via a spacer which contains at least one of the following groups: thioether, dissulfide, and thiosuccinimidyl.

Suitable polyoxoanions have the formula —$OMO_n$ and —$MO_n$, where M may be S or P and n is an integer of from 2 to 3, and include sulfate, sulfonate, sulfinate, phosphate and phosphonate. These groups are easily introduced into amino acids and/or the amino acid residues of polypeptides. For example, sulfate groups may be introduced into tyrosine by the reaction with sulfuric acid at low temperatures (Reitz et al, *J. Am. Chem. Soc.*, vol. 68, p. 1024 (1946) and Kohli et al, *FEBS Lett.*, vol. 242, pp. 139-143 (1988)) and may be introduced into tyrosine residues of polypeptides by the use of concentrated sulfuric acid (Ondetti et al, *J. Am. Chem. Soc.*, Vol. 92, pp. 195-199 (1970). Sulfonate groups may be introduced by either the conversion of the free sulfhydryl groups of cysteine residues to S-sulfo-derivatives by treatment with sodium tetrathionate, $Na_2S_4O_6$ (Dixon et al. *Nature*, vol. 188, p. 721 (1960)) or peptides containing disulfide linkages can be reduced with dithiothreitol followed by treatment with sodium tetrathionate (Inglis et al, *J. Biol. Chem.*, vol. 245, p. 112 (1970)). In addition, 3-sulfino-L-alanine is available from Aldrich and may be incorporated in the oligopeptide backbone.

Phosphate groups may be introduced by a variety of methods. Thus, tyrosine may be converted to the O-phosphate derivative by reaction with $P_2O_5$ in $H_3PO_4$ (Rothberq et al, *Proc. Natl. Acad. Sci. USA*, vol. 75, pp. 4868–4872 (1978)) or serine may be converted to phosphoserine by treatment with $POCl_3$ (Neuhaus et al, *Biochem. Prepn.*, vol. 6, p. 75 (1958)). Alternatively, phosphothreonine is commercially available and may be used as a starting amino acid for the production of the polypeptide oligomer backbone. In addition, histidine can be derivatized to τ-phosphohistidine by reaction with phosphoamidate (Hulquist et al, *Biochemistry*, vol. 5, p. 22 (1966) and Fujitaki et al, *Meth. Enzymol.*, vol. 107, pp. 23–26 (1984)), and arginine can be derivatized to ω-N-phosphoarginine by reaction with phosphorus oxychloride (Thiem et al, *Bull. Soc. Chim. Biol.*, vol. 5, p. 322 (1962) and Fujitaki et al, *Meth. Enzymol.*, vol. 107, pp. 23–26 (1984)).

Phosphonate moieties may be introduced into polypeptide oligomers by the reaction of the free sulfhydryl groups of cysteine residues with a phosphonic acid derivative, generated by the reaction of 3-aminopropyl-phosphonic acid with iodoacetic anhydride (*Meth. Enzymol.*, vol. 11, p. 532 (1967)).

In addition to the methods described above, phosphate groups may be introduced into polypeptides by the enzymatic phosphorylation of amino acid residues in polypeptides. For example, casein kinase of type II and cAMP-dependent kinases phosphorylate serine, while casein kinases of type I phosphorylate threonine and, to a lesser extent, serine. Another group of kinases exhibits strict specificity for tyrosine (Corbin and Hardman, eds., *Meth. Enzymol.*, vol. 99, Part F, Protein Kinases (1983)).

Similarly, amino acid residues in polypeptides may be enzymatically sulfonated. Thus, tyrosylprotein sulfotransferase catalyzes the sulfonation of proteins at tyrosine residues (Lee et al, *J. Biol. Chem.*, vol. 258, p. 11326 (1983) and Huttner, *Meth. Enzymol.*, vol. 107, pp. 200–233 (1984).

It is preferred that the polyoxoanion is sulfonate.

The polyoxoanion groups may be present as free acids or may be partially or totally neutralized. In the salts formed by partial or total neutralization of the free acid form of the polyoxoanion, the cation may be any suitable ion such as a metal ion or an ammonium ion. Suitable metal ions are those that do not negate the water solubilizing effect of the polyoxoanion and include alkali metals such as lithium, sodium, potassium; alkaline earth metals such as magnesium, calcium, etc.; and transition metals such as, e.g., iron, copper, zinc, etc. Suitable ammonium ions include $NH_4^+$ and those in which one or more of the hydrogens have been substituted by an organic group, such as, e.g., tetramethylammonium.

The functional groups which serve to bond the fluorescent or chemiluminescent labels are suitably any of the reactive functional groups found in R of the naturally occurring amino acids, e.g., $-NH_2$ in lysine (Lys); $-NHC(NH_2)=NH$ in arginine (Arg); $-CONH_2$ in asparagine (Asn) and glutamine (Gln); $-OH$ in serine (Ser), threonine (Thr), and tyrosine (Tyr); and $-CO_2H$ in aspartic acid (Asp) and glutamic acid (Glu). It is preferred that the functional group be one of either $NH_2-$ and $-CO_2H$, so that one terminus of the polypeptide backbone may also be conveniently used as one of the sites for bonding the fluorescent or chemiluminescent label.

It is to be understood that the $-NH_2$ groups in R of e.g., Lys and the $-NH_2$ terminal position; the $-CONH_2$ groups in R of Asn and Gln; the $-NHC(NH_2)=NH$ group in R of Arg; and the imidazole group in R of His are sufficiently dissimilar in reactivity to be classified as different reactive groups for the purposes of the present invention. In other words, the presence of an Asn or Arg residue in the oligopeptide backbone does not prevent the terminal $-NH_2$ from serving as the unique functional group to bond the ligand or receptor.

Specific examples of suitable chemiluminescent labels are disclosed in German OLS No. 2,618,511, U.S. Pat. No. 4,331,808, and Haugland, *Handbook of Fluorescent Probes and Research Chemicals*, Molecular Probes, Inc., Eugene, Oregon (1989) which are incorporated herein by reference. Thus, suitable labels include luminol, isoluminol, pyrogallol, luciferin, and naphthalene-1,2-dicarboxylic acid hydrazide derivatives. These labels may be attached to the oligopeptide backbone by conventional methods. For example, a polypeptide may be labeled with a 7-aminonaphthalene-1,2-dicarboxylic acid hydrazide derivative by condensation of any $-CO_2H$ groups on the oligopeptide backbone with a compound of the formula:

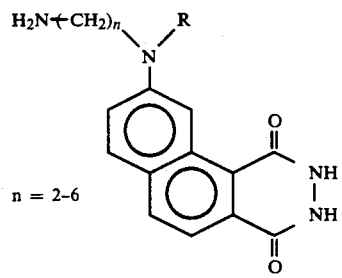

as disclosed in U.S. Pat. No. 4,331,808.

Specific examples of suitable fluorescent labels are those disclosed in Blecka et al, "Immunoassays in Therapeutic Drug Monitoring," *Clinics in Laboratory Medicine*, vol. 7, pp. 357–370 (1987) and Haugland, *Handbook of Fluorescent Probes and Research Chemicals*, Molecular Probes, Inc., Eugene, Oreg. (1989), which are incorporated herein by reference, and include, e.g., fluorescein, rhodamine, anthracene and fluorescamine. Again, the fluorescent labels may be attached to the oligopeptide backbone by conventional methods. For example, fluorescein labels may be bonded to a polypeptide which contains a plurality of $-CO_2H$ groups by first treating the polypeptide with carbohydrazide, to obtain a carbohydrazide derivative, followed by treating the carbohydrazide derivative with fluorescein isothiocyanate (FITC). This procedure is shown schematically below:

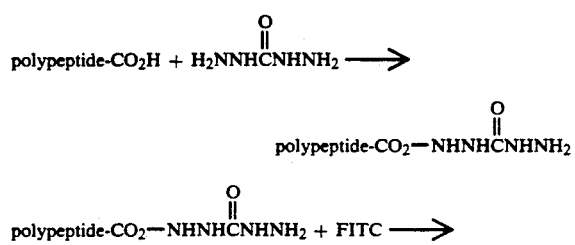

Similarly, rhodamine X isothiocyanate and 2-anthraceneisothiocyanate may be coupled with the carbohydrazide derivative.

Further examples of labels include ruthenium complexes such as those described in U.S. Pat. No. 4,745,076, incorporated herein by reference. These labels are particularly suitable for time-resolved measurements (U.S. Pat. No. 4,745,076) and electrogenerated chemiluminescent measurements (Ege et al, *Analytical Chem.*, vol. 56, 2413 (1984) and Zhang et al, *J. Phys. Chem.*, vol. 92, 5566 (1988)).

In regard to the number and distribution of the polyoxoanion groups and the groups for bonding the labels, it is preferred that there be at least two of each of these types of groups. It is especially preferred that there be at least three of both the polyoxoanions and the groups for bonding the label. It is also preferred that the ratio of the number of polyoxoanions to the number of the functional groups for bonding the labels fall within the range of 1:4 to 4:1, more preferably 1:2 to 2:1. In the interest of signal strength, it is preferred to keep the number of labels in the molecule relatively high. However, as the ratio of labels to anions in the molecule increases, the hydrophilicity and solubility decrease and the likelihood of signal quenching also increases. In this regard, a suitable degree of labeling in the present molecules, and thus a suitable occurrence of groups for bonding the label, is on average about one label per 3 to 10 amino acid residues. A similar degree of substitution is suitable for the polyoxoanion.

It is to be understood that neither the functional groups for bonding the label nor the polyoxoanions need be spaced with strict regularity along the polypeptide backbone. Rather, it is only required that the labels be spaced sufficiently far apart to avoid quenching and that the polyoxoanions be spaced such as to impart the desired hydrophilicity/solubility.

The amino residues contained in the backbone may be any of the naturally occurring α-amino acids represented by the formula $H_2N—CH(R)—CO_2H$, such as glycine (Gly), alanine (Ala), valine (Val), leucine (Leu), isoleucine (Ile), methionine (Met), proline (Pro), phenylalanine (Phe), tryptophan (Trp), serine (Ser), theronine (Thr), cysteine (Cys), tyrosine (Tyr), asparagine (Asn), glutamine (Gln), aspartic acid (Asp), glutamic acid (Glu), lysine (Lys), arginine (Arg), and histidine (His). The content and sequence of the amino acids are limited only by the need to satisfy the requirement of providing the three types of functional groups discussed above.

For example, if the terminal $—NH_2$ group of the polypeptide oligomer is to serve as the unique functional group for bonding to the ligand, then the polypeptide oligomer should not contain any amino acid residues which contain $—NH_2$ groups in R, such as, for example, lysine. Similarly, when the terminal $—CO_2H$ group is to serve as the unique functional group, the backbone should contain no residues which contain $—CO_2H$ in R. On the other hand, a polypeptide which contains a plurality of aspartic acid or glutamic acid residues will provide a number of $—CO_2H$ groups which can serve to bond the fluorescent or chemiluminescent label.

Thus, the oligopeptide backbone may be either a naturally occurring or synthesized oligopeptide. The synthetic oligopeptide backbone may be synthesized by any conventional procedure. In particular, solid state synthesis utilizing any of the commercially available instruments, such as that produced by Applied Biosystems of Foster City, CA, is suitable. A discussion of the solid state synthesis of oligopeptides is provided in U.S. Pat. No. 3,531,258, which is incorporated herein by reference.

Alternatively, the oligopeptide may be synthesized by recombinant DNA technology. That is, the gene encoding for the desired oligopeptide may be synthesized or isolated and then inserted into a suitable cloning vector which is used to transform a suitable host. The production of oligopeptides by recombinant DNA technology is discussed in U.S. Pat. Nos. 4,704,362, 4,652,525 4,431,740, 4,440,859, and 4,342,832, which are incorporated herein by reference.

The present conjugates may be assembled by first introducing the polyoxoanion groups into the oligopeptide backbone, followed by bonding the ligand or receptor to the unique functional group and then attaching the labels to the remaining functional groups. Alternatively, the labels may be attached to the backbone before the ligand or receptor is attached or the polyoxoanions may be introduced after either of the other two steps. Thus, in one embodiment, the present invention relates to an intermediate ligand compound which is an oligopeptide, bonded to a ligand or receptor, in which at least one of the amino acid residues has been converted to a polyoxoanion derivative and a plurality of the amino acid residues contain a functional group for bonding a fluorescent or chemiluminescent label. In another embodiment, the present invention relates to an intermediate labeled compound which is an oligopeptide, in which at least one of the amino acid residues has been converted to a polyoxoanion derivative, a plurality of the amino acid residues are linked to a fluorescent or chemiluminescent label, and having a unique functional group for bonding a ligand or receptor.

These intermediate compounds may be represented by the general formulae

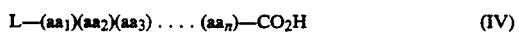 (IV)

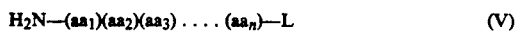 (V)

wherein L and n are as defined above and at least one of the amino acid residues contains a polyoxoanion of phosphorus or sulfur and a plurality of the amino acid residues have a functional group for bonding a chemiluminescent or fluorescent label; or

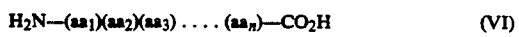 (VI)

wherein n is as defined above and at least one of the amino acid residues contains a polyoxoanion of phosphorus or sulfur and a plurality of the amino acid residues are bonded to a chemiluminescent or fluorescent label.

Examples of suitable oligopeptide backbones include the insulin A-chain and fragments of cholecystokinin-pancreozymin which may be sulfated as disclosed in Ondetti et al, *J. Am. Chem. Soc.*, Vol. 92, pp. 195–199 (1970) some of which are shown below.

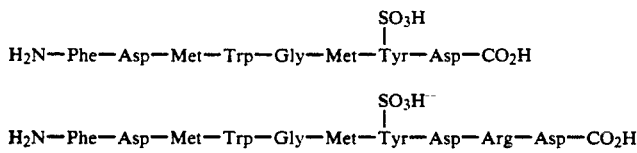

A preferred embodiment of the oligopeptide backbone of present conjugates is represented by insulin A-chain or a polypeptide having substantially the same number of amino acid residues and molecular weight as insulin A-chain, with one terminal amino or carboxy group for covalent attachment of a ligand or receptor molecule, at least two functional groups for covalent attachment of a label at a distance from the ligand or receptor site sufficient to minimize quenching of the labels by the ligand or receptor, and at least two functional groups which may be converted to a polyoxoanion of phosphorus or sulfur. Such oligopeptides include insulin A-chain; oligopeptides having substantially the same number of amino acid residues as insulin A-chain, at least two cysteine residues and at least one amino acid residue having a —$CO_2H$ group in R, such as Glu or Asp, but only one —$NH_2$ group; and oligopeptides having substantially the same number of amino acid residues as insulin A-chain, at least two cysteine residues, and at least one amino acid residue having a —$NH_2$ group in R, such as Lys, but only one —$CO_2H$ group. Examples of such peptides may be represented by the formula $$H_2N—(aa_1)(aa_2)(aa_3)\ldots(aa_n)—CO_2H \qquad (VII)$$

in which n is about 21, at least two of the amino acid residues are cysteine, at least one of the amino acid residues has a —$CO_2H$ group in R, such as Glu or Asp, and none of the remaining amino acid residues have —$NH_2$ groups in R, such as Lys; or n is defined as above, at least two of the amino acid residues are cysteine, at least one of the amino acid residues has a —$NH_2$ group in R, such as Lys, and none of the remaining amino acid residues contain a —$CO_2H$ group in R, such as Glu or Asp.

The A-chain of insulin represents an ideal backbone for the synthesis of a sulfonated oligomeric carrier molecule. The A-chain of insulin is a hydrophilic peptide containing 21 amino acid residues and has a molecular weight of approximately 2500 daltons.

Four of the amino acids are cysteine residues with a free sulfhydryl group which can easily be derivatized to S-sulfonates, *J. Am. Chem. Soc.*, vol. 88, 5625–5635 (1966). Two carboxyl groups from glutamate residues 4 and 17 and one terminal carboxyl group from an asparagine residue provide three sites for attachment of fluorescent or chemiluminescent molecules. The insulin A-chain contains one terminal amino group for covalent attachment of a single ligand or receptor molecule. Since the sites for attachment of the fluorescent or chemiluminescent labels are 4, 17, and 21 amino acid residues away from the ligand or receptor attachment site, the possibility of quenching of the labels by the ligand or receptor is minimized.

Thus, insulin A-chain in the tetra-S-sulfonate form may be easily coupled to an antigen, such as the dinitrophenyl group, via the terminal —$NH_2$ group by reaction with 1-fluoro-2,4-dinitrobenzene, to obtain dinitrophenyl-insulin A-chain (DNP-insulin A-chain). Derivatization of the carboxyl groups of DNP-insulin A-chain with carbohydrazide, followed by reaction with fluorescein isothiocyanate (FITC) gives DNP-insulin A-chain-fluorescein (DNP-Ins-Fl), the structure of which is shown below:

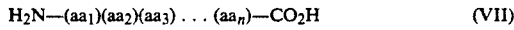

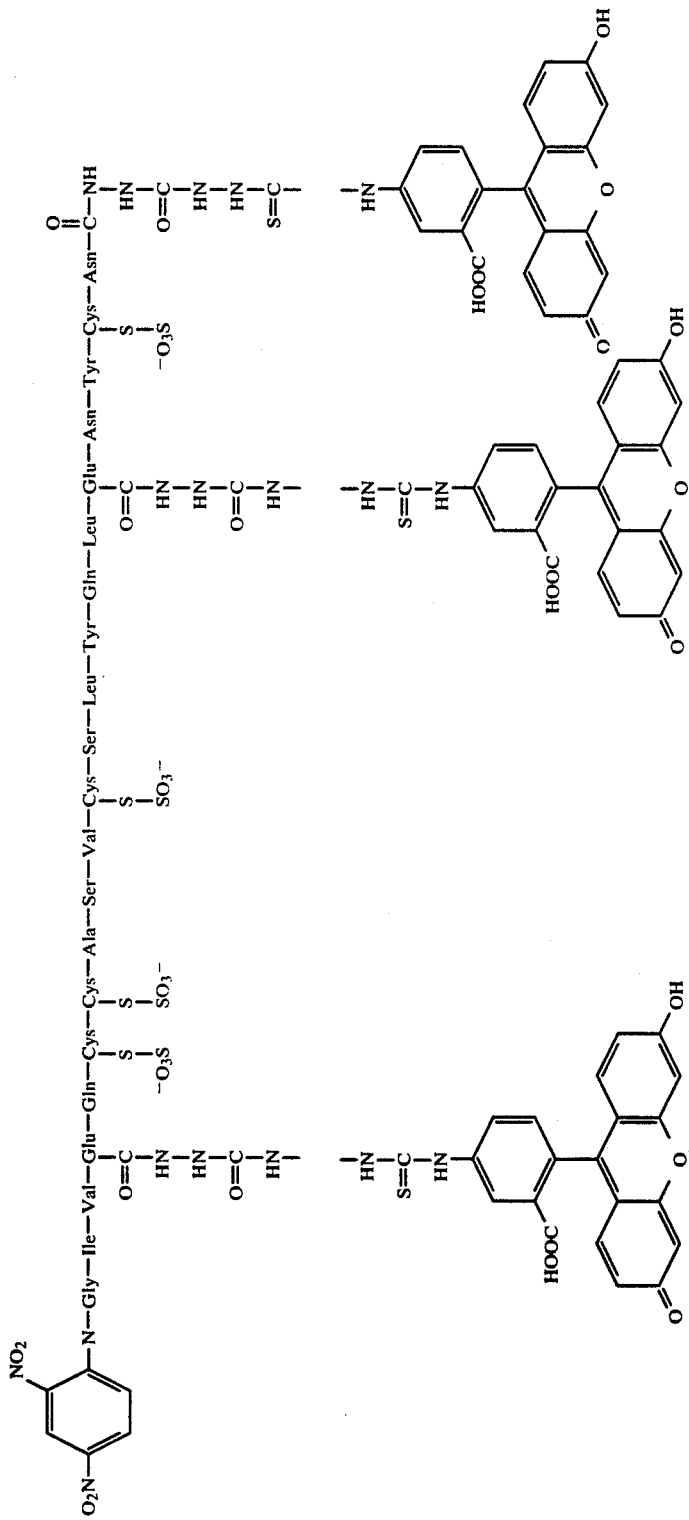

The ligand-insulin A-chain-fluorescein conjugates (Ligand-Ins-Fl) are ideally suited for use in assays for the free ligand. For example, the amount of non-specific binding of DNP-Ins-Fl to immobilized anti-DNP IgG (antibody #51) is only about one-third that of a conjugate in which a dinitrophenyl group is linked to fluorescein via a lysine residue, DNP-lys-fluorescein (DNP-Lys-Fl) (see Table II). Further, the amount of DNP-Ins-Fl specifically bound to antibody #51 is about 1.7-fold higher than that of DNP-Lys-Fl.

Figure 3:
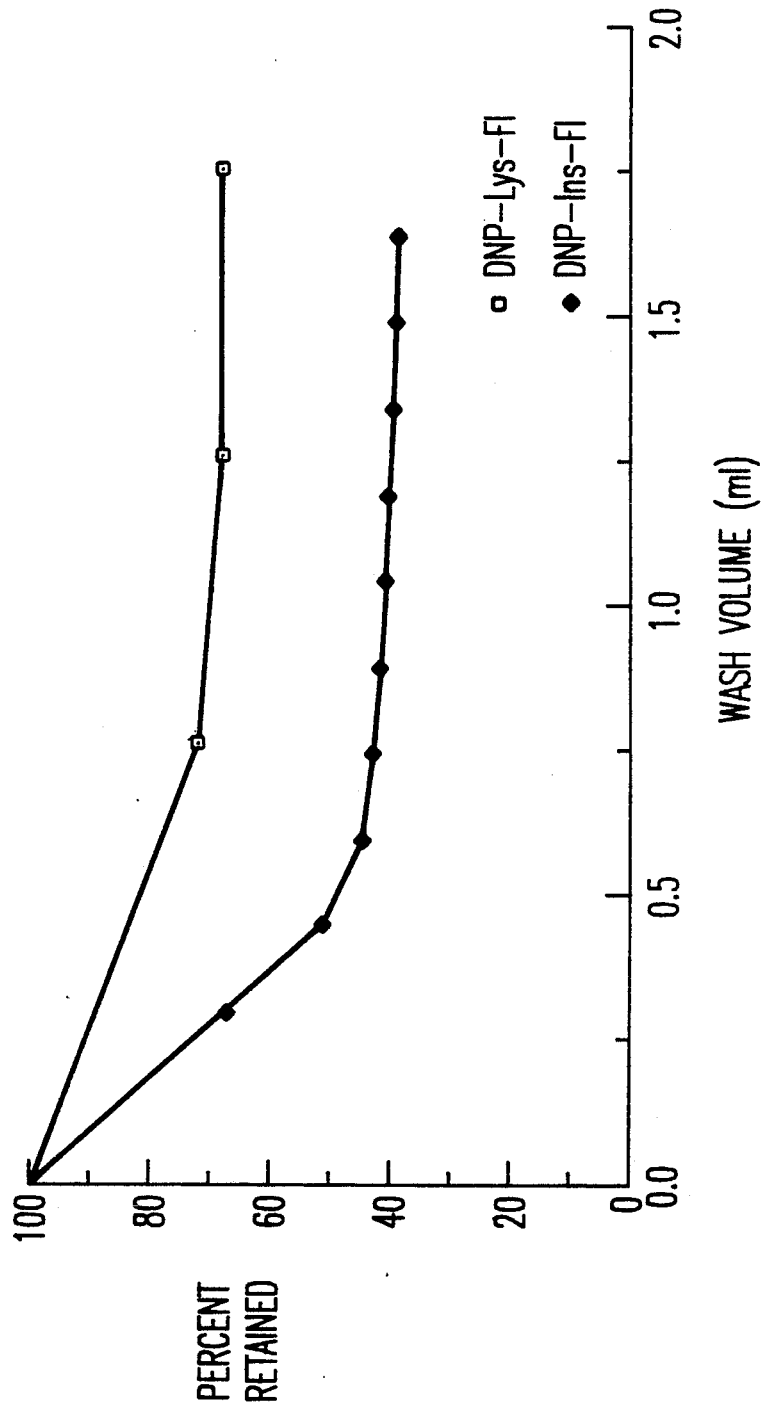
FIG. 3 illustrates the binding of different DNP-conjugates to immobilized monoclonal anti-DNP antibody 51.

In FIG. 3 the binding of the different DNP conjugates to anti-DNP-Sepharose at a 3:1 molar ratio of conjugate to immobilized antibody is shown. After extensive washing of the matrix, a 1.6-fold difference in binding of DNP-Lys-Fl (62.7%) versus DNP-Ins-Fl (38.8%) was observed. In a attempt to identify the factors contributing to this significant difference, the binding of DNP-Ins without attached fluorescein molecules was also determined. The data in Table II reveal an almost identical extent of binding of DNP-Ins and DNP-Ins-Fl to anti-DNP-Sepharose, suggesting that the increased number of fluorophores in the DNP-Ins-Fl conjugate compared to the DNP-Lys-Fl conjugate is not a critical factor.

In order to determine whether the differences in the extent of binding shown in FIG. 3 are a result of a different affinity of the immobilized anti-DNP antibody for both conjugates, DNP-Ins-Fl and DNP-Lys-Fl, the displacement of the different DNP conjugates from the antigen binding sites of immobilized anti-DNP antibody #51 by DNP-lysine was determined. The analyses revealed that under comparable conditions, the displacement of DNP-Ins-Fl is much more efficient than that of DNP-Lys-Fl (see Table III). However, the data in Table III also demonstrate that the displacement of DNP-Ins-Fl is two-fold more efficient than that of DNP-Ins, whereas the extent of binding of DNP-Ins-Fl and DNP-Ins was almost identical (Table II). Therefore, a difference in affinity cannot be the only factor responsible for the different binding efficiencies of the DNP conjugates to anti-DNP-Sepharose.

Table II compares the extent of binding of the different DNP conjugates to immobilized anti-DNP IgG (antibody #51) with that to immobilized non-immune IgG. The data show that the extent of non-specific binding of DNP-Lys-Fl to immobilized non-immune IgG is three-fold higher than that of DNP-Ins-Fl. After subtraction of non-specific binding to non-immune IgG-Sepharose from binding to anti-DNP-Sepharose, a fundamentally different binding pattern becomes evident. The amount of DNP-Ins-Fl that specifically is bound to the antigen binding sites of immobilized antibody #51 (0.7 mole conjugate/mole antibody) is 1.7 fold higher than that of DNP-Lys-Fl (0.4 mole conjugate/mole antibody). These results show that the different extent of binding of DNP-Lys-Fl and DNP-Ins-Fl to anti-DNP-Sepharose given in FIGS. 3 is a consequence of the high nonspecific binding of DNP-Lys-Fl.

In another aspect, the present invention relates to kits which contain the present conjugates and/or intermediate compounds. Such kits may take any form that is suitable for the employment of the present conjugates and/or intermediate compounds in an assay for a ligand and/or receptor. In particular, the present kits may contain a vial or other container which may contain the present conjugate and/or intermediate compound in solution or powdered form. If the present conjugate and/or intermediate compound is in solution form, the solution may also contain other materials, such as, e.g., a preservative, buffer, salt, etc. The kit may also contain a standard sample of either the ligand or receptor of the present conjugate or the binding complement of the ligand or receptor. Such standard samples may be in the form of a solution of known concentration and/or activity or a sample of known weight and/or activity. In addition, the present kits may contain samples in which the binding complement of the ligand or receptor of the conjugate is immobilized on a solid support, such as a glass slide, glass beads, gelatin beads, polymer matrix, etc.

The present conjugates and kits are useful for assaying ligands or receptors and/or the binding complements of the ligands or receptors, in specific binding assays in which the displacement or competitive-binding of the present conjugates are used to determine the amount or concentration of the free ligand or receptor (or complement thereof) present in a sample. The sample may be of biological or nonbiological origin and may be originally obtained in gaseous, liquid or solid form.

Other features of the invention will become apparent in the course of the following descriptions of exemplary embodiments which are given for illustration of the invention and are not intended to be limiting thereof.

General Methods

Fluorescence intensity was measured on a SLM 8000 fluorimeter at 490 nm excitation and 519 nm emission. Individual fluorescence standard curves with known concentrations of the different DNP-fluorescein conjugates were used to calculate the amounts of DNP-conjugates from fluorescence units. Antibodies were coupled to tresyl chloride-activated Sepharose 4B (Sigma) at a concentration of 200 ug antibody/100 mg gel according to the manufacturer's recommendation. The amount of immobilized antibody was determined using a Coomassie blue assay as described in Ahmad et al, *Anal. Biochem.*, vol. 148, pp 533–541 (1985). Peptide and protein determinations in fluid-phase were performed by UV absorbance at 280 nm, by the bicinchoninic acid method (Smith et al, *Anal. Biochem.*, vol. 150, pp. 76–85 (1985)) using the Pierce BCA Protein Assay Reagent (Pierce), and by the Folin-Ciocalteau method (Lowry et al, *J. Biol. chem.*, vol. 193, pp. 265 (1951)). The A-chain of bovine insulin (oxidized to the S-sulfonate form) (Sigma), the DNP-Ins conjugate, and the DNP-Ins-Flu conjugate were radiolabeled with Na$^{125}$I (Amersham, Arlington Heights, IL) using immobilized chloramine-T (Iodo-Beads; Pierce, Rockford, IL) (Petrella et al, *J. Immunol. Methods*, vol. 104, pp. 159–172 (1987)).

Synthesis of the DNP-Insulin A-Chain-Fluorescein Conjugate

The synthesis was performed in three steps: 1) coupling of 1-fluoro-2,4-dinitrobenzene (FDNB) to the terminal amino group of the insulin A-chain oxidized to the tetra-S-sulfonate form, 2) derivatization of the carboxyl groups with carbohydrazide, and 3) coupling of fluorescein isothiocyanate (FITC) to the hydrazide derivative of DNP-insulin A-chain.

Step 1

Insulin A-chain in the tetra-S-sulfonate form (Sigma, St. Louis, MO) (25 mg; approximately 8 μmoles), mixed with $^{125}$I-labeled S-sulfonated insulin A-chain (26 nmole, $5 \times 10^7$ cpm), was incubated with 50 μmol (9.3 mg) of FDNB (Aldrich, Milwaukee, WI) in a total volume of 6.4 mL containing 100 mM NaHCO$_3$ and 19% (v/v) ethanol. After two hours of incubation at 37° C., the reaction mixture was subjected to Sephadex G-10 size exclusion chromatography to remove non-coupled FDNB molecules were lyophilized and stored at −20° C. The ratio of coupled FDNB residues per insulin A-chain was calculated from the specific radioactivity of the peptide and the UV absorbance at 365 nm using an extinction coefficient of $1.6 \times 10^4$ M$^{-1}$cm$^{-1}$ (Hirs, *Meth. Enzymol.*, XI, pp. 548–555 (1967)). Preparations containing less than one DNP residue per insulin A-chain were subjected to a second derivatization with freshly added FDNB as described above.

Step 2

DNP-derivatized insulin A-chain (tetra-S-sulfonate form) (DNP-Ins) (3.5 mg; approximately 1.2 μmol) was dissolved in 800 μl of 10 mM sodium phosphate-150 mM NaCl, pH 7.4. After the addition of 165 mg (1.8 mmol) of carbohydrazide (Aldrich) and 20 mg (0.1 mmol) of 1-ethyl-3-(3-dimethylaminopropyl)-carbodiimide (EDC) (Sigma), the pH was adjusted to pH 5.0 with hydrochloric acid. The reaction mixture (total volume 950 μl) was incubated at room temperature for 18 hours (the pH was maintained at 5.0) and then subjected to Sephadex G-10 size exclusion chromatography. The peptide fraction, eluted with 19% (v/v) ethanol in H$_2$O, was lyophilized and stored at −20° C.

Step 3

Carbohydrazide-derivatized DNP-insulin A-chain (tretra-S-sulfonate form) (0.35 mg; approximately 0.1 nmol) was dissolved in 950 μl of 50 mM NaHCO$_3$ containing 19% (v/v) ethanol. FITC (Aldrich) (16 mg; 41 μmol) was added, and after 18 hours of incubation at room temperature in the dark, the reaction mixture was subjected to Sephadex G-10 size exclusion chromatography. The peptide fraction, eluted with 19% (v/v) ethanol in H$_2$O, was lyophilized, redissolved in 50 mM NaHCO$_3$ containing 19% (v/v) ethanol, and rechromatographed on Sephadex G-10 to remove traces of any non-covalently bound fluorophores. The number of covalently attached fluorescein molecules was spectrophotometrically determined at 494 nm using an extinction coefficient of $7.6 \times 10^4$ M$^{-1}$cm$^{-1}$ (Wilderspin et al, *Anal. Biochem.*, vol. 132, pp. 449–455 (1983)).

Spectrophotometric analyses of the purified DNP-insulin-A-chain-fluorescein conjugate (DNP-Ins-Fl) confirmed the theoretical ratio of one DNP residue and three fluorescein residues per insulin A-chain molecule as shown below in Table I.

TABLE I

| Molar ratio of covalently attached FDNB and FITC molecules per insulin A-chain. | | |
|---|---|---|
| Derivatization of insulin A-chain with: | Ratio: modifying residue/insulin A-chain | |
| | Expected | Found |
| FDNB | 1.0 | 1.1 ± 0.1 |
| FITC | 3.0 | 3.2 ± 0.1 |

Synthesis of the DNP-Lysine-Fluorescein Conjugate

ε-DNP-L-lysine hydrochloride (Research Organics Inc., Cleveland, Ohio 44125) (10 mg; 0.029 mmol) was dissolved in 1.0 ml of 0.5 M NaHCO$_3$ and adjusted to pH 9.3 with NaOH. Fluorescein isothiocyanate (Aldrich) (10 mg; 0.026 mmol) was added, and the reaction mixture (total volume 1.2 ml) was incubated in the dark for 30 min at room temperature. Purification of the synthesized DNP-lysine-fluorescein conjugate (DNP-Lys-Fl) was performed by reverse phase HPLC on an Ultrasphere ODS C-18 column (Beckman, CA) at a flow rate of 0.75 ml/min using a linear gradient from 5% (v/v) methanol (in H$_2$O) to 100% methanol (within 15 min). The DNP-Lys-Fl conjugate fractions from several chromatographic runs were combined, lyophilized, and stored at −20° C. Rechromatography of an aliquot of the combined fractions under identical conditions demonstrated 95% purity of the DNP-Lys-Fl conjugate. The structure of DNP-Lys-Fl is shown below.

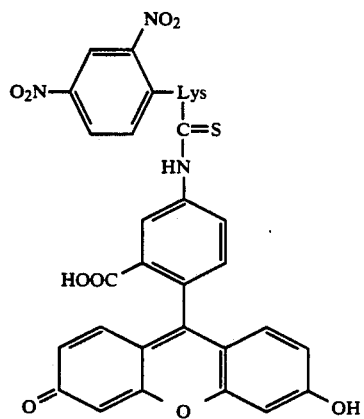

Determination of Fluorescence Lifetime

The fluorescence lifetime of the DNP-fluorescein conjugates was measured on an ISS Greg-200 variable frequency phase fluorimeter as described previously (Lakowicz et al, *Biophys. J.*, vol. 46, pp. 463–477 (1984) and Gratton et al, *Biophys. J.*, vol. 46, pp. 479–486 (1984)) using 1-chloro-bis-(phenylethynyl)anthracene (Aldrich) in ethanol (3.791 ns) as a reference (Thompson et al. *Anal. Chem.*, vol. 60, pp. 670–674 (1988)). The resulting phase and modulation data for DNP-Ins-FL were fit to one, two, and three emissive components using a Simplex algorithm supplied by ISS. The results are shown in FIG. 1. The data fitted best ($X^2 = 1.26$) to two components: the first comprises about two thirds of the mixture and exhibited a lifetime corresponding closely to that of fluorescein (4.091 ± 0.177 ns; 64 ± 7%), and a shorter lifetime component comprising about one third of the mixture (2.068 ± 0.150 ns; 36%). Fitting these data to one component gave an unacceptable $X^2$ ($X^2 = 33$) and non-random differences between the data and calculated values. When the data were fit to a three component model, the third component was weak (<5%), poorly defined (1.1 ± 3.2 ns), and gave no improvement in $X^2$. Therefore, a third component appears to be unnecessary to fit the data. Since the DNP moiety has the ability to quench the fluorescein emission, the data are best explained by two fluorescein residues being remote from and unquenched by the DNP group with the third fluorescein residue being closer and subject to quenching. In accord with this explanation is the observation that the fluorescence of the DNP-lysine-fluorescein derivative was substantially quenched as shown by its reduced quantum efficiency and subanosecond fluorescence lifetime.

Figure 2:
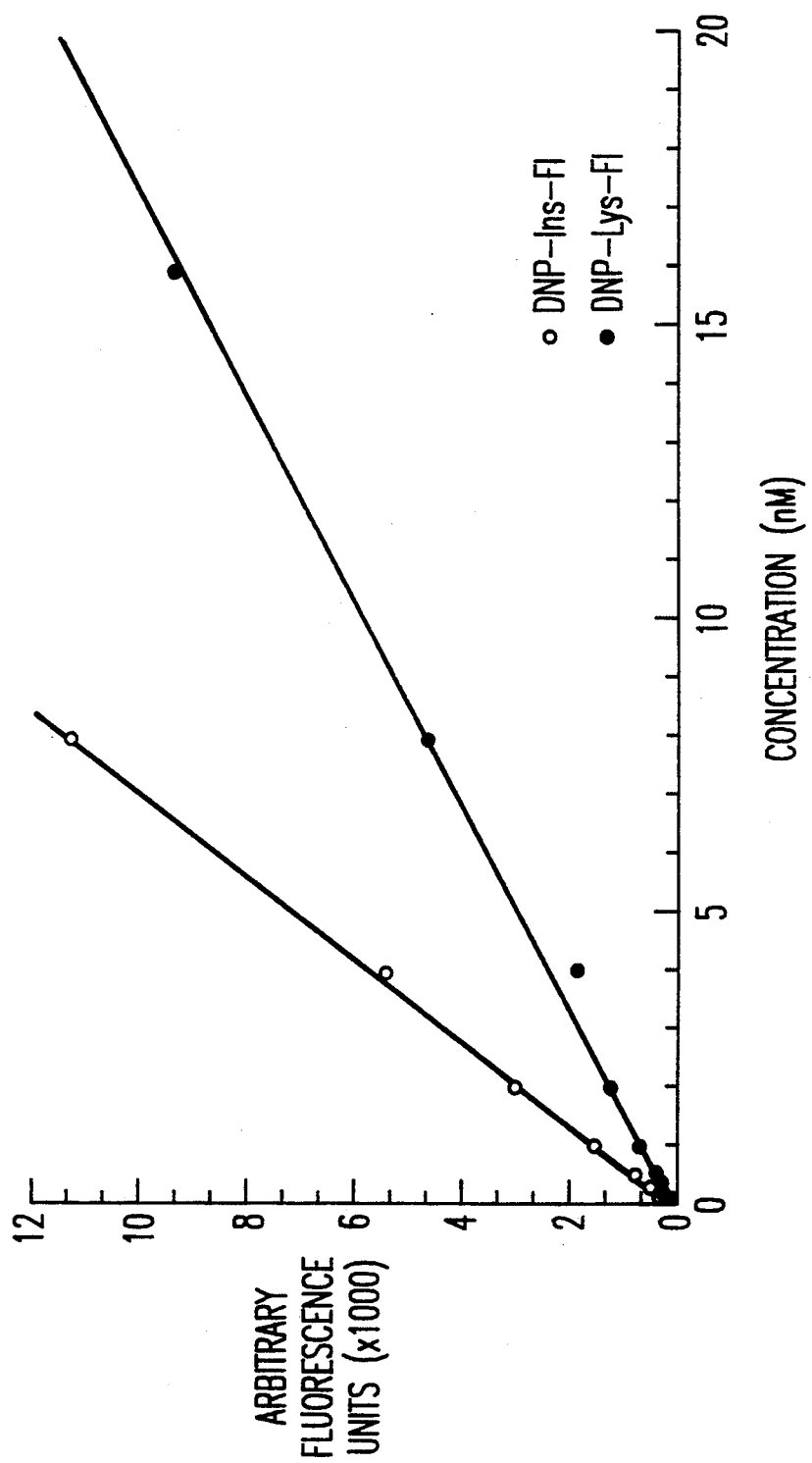
FIG. 2 illustrates the relationship between the fluorescence intensity and concentration of the DNP-insulin A-chain-fluorescein conjugate and the DNP-lysine-fluorescein conjugate.

In addition, the relationship between the fluorescence intensity and concentration for DNP-Ins-Fl and DNP-Lys-Fl is given in FIG. 2.

Specific and Nonspecific Binding of DNP-Conjugates

Specific binding of the DNP-conjugates was determined with the murine monoclonal anti-DNP antibody #51 (Stanley et al, *J. Immunol. Methods*, vol. 64, pp. 119–132 (1983) and Steward et al, *J. Immunol. Methods*, vol. 78, pp. 173–190 (1985)) coupled to tresyl chloride-activated Sepharose 4B (anti-DNP-Sepharose) The monoclonal IgG1 antibody #51 (purified from ascites) was kindly provided by Dr. M. W. Steward (Dept. of Medical Microbiology, London School of Hygiene and Tropical Medicine, London, U.K.). Nonspecific binding was measured with Sepharose 4B-immobilized non-immune mouse IgG purified from mouse serum (Jackson ImmunoResearch Laboratories, West Grove, PA) (IgG-Sepharose). After removal of buffer by vacuum filtration on a scintered glass funnel, 50 mg aliquots of Sepharose 4B-antibody matrices were transferred to plastic conical vials and incubated with $^{125}$I-labeled DNP-insulin A-chain-fluorescein conjugate ($1.6 \times 10^6$ cpm/nmole), or $^{125}$I-labeled DNP-insulin A-chain conjugate without attached fluorescein residues ($3.3 \times 10^6$ cpm/nmole), or non-radiolabeled DNP-Lys-Fl at a 3 to 1 molar ratio of DNP-derivative to immobilized IgG in 10 mM phosphate/150 mM NaCl, pH 7.6, overnight at 4° C. on a rocking platform. Unbound conjugate was recovered by poking a hole in the bottom of the plastic vial with a 30 gauge needle, loading the vial on the top of a glass test tube, and centrifuging. Subsequent washing steps were performed with 150 μl of 10 mM phosphate/150 mM NaCl/0.1% (v/v) Triton X-100, pH 7.6. Aliquots of the solutions collected in the bottom of the test tubes after centrifugation were assayed for radioactivity or fluorescence. The results are shown in Table II and FIG. 3.

TABLE II

Specific and nonspecific binding of DNP-conjugates.

| DNP-Conjugate | DNP-Conjugate Applied (nmoles) | Ratio of Applied DNP-Conjugate to Immobilized IgG (moles/moles) | DNP-Conjugate Bound (nmoles) | Ratio of Bound DNP-Conjugate to Immobilized IgG (moles/moles) |
|---|---|---|---|---|
| I. Binding to anti-DNP IgG1 | | | | |
| DNP-Lys-Fl | 0.59 | 3.0 | 0.37 ± 0.02 | 1.9 |
| DNP-Ins-Fl | 0.29 | 3.0 | 0.11 ± 0.03 | 1.2 |
| DNP-Ins | 0.29 | 3.0 | 0.11 ± 0.01 | 1.2 |
| II. Binding to non-immune IgG | | | | |
| DNP-Lys-Fl | 2.60 | 3.0 | 1.27 ± 0.07 | 1.5 |
| DNP-Ins-Fl | 2.53 | 3.0 | 0.44 ± 0.16 | 0.5 |

Specificity and Effectivity of Displacement of DNP-Conjugates

Aliquots of anti-DNP-Sepharose (50 mg) were incubated with $^{125}$I-labeled DNP-insulin A-chain, or $^{125}$I-labeled DNP-insulin A-chain-fluorescein, or DNP-lysine-fluorescein and washed with 10 mM phosphate/150 mM NaCl/0.1% (v/v) Triton X-100, pH 7.6 , as described above in Specific and Nonspecific Binding of DNP-Conjugates. When the wash solutions showed background levels of radioactivity or fluorescence, 150 μl of 10 mM phosphate/150 mM NaCl/0.1% (v/v) Triton X-100, pH 7.6, containing the compound to be tested for displacement of antibody-bound DNP-conjugate was added to the anti-DNP-Sepharose aliquots, and centrifuged as described. Displacement was determined by assaying aliquots of the solutions collected in the bottom of the test tubes after centrifugation for radioactivity or fluorescence. The results are shown in Table III.

TABLE III

Displacement of DNP-conjugates from immobilized monoclonal anti-DNP antibody by DNP-lysine.

| Antibody-Bound DNP-Conjugate | Ratio of Free DNP-Lysine to Antibody-Bound DNP-Conjugate [mole/mole] | Displacement of Antibody-Bound DNP-Conjugate by DNP-Lysine [pmole ± S.D.] |
|---|---|---|
| DNP-Lys-Fl | 2.0 | 0.45 ± 0.14 |
| DNP-Ins-Fl | 3.4 | 3.20 ± 0.70 |
| DNP-Ins | 3.4 | 1.56 ± 0.01 |

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A ligand-label conjugate, which is an oligopeptide of 5 to 100 amino acid residues, which is bonded to a ligand or receptor, wherein at least one of said amino acid residues contains a polyoxoanion of sulfur or phosphorus and a plurality of said amino acid residues are linked to a chemiluminescent or fluorescent label.

2. The conjugate of claim 1, wherein the number of amino acid residues in said oligopeptide is from 10 to 50.

3. The conjugate of claim 1, wherein the number of amino acid residues in said oligopeptide is from 15 to 25.

4. The conjugate of claim 1, wherein said label is selected from the group consisting of luminol, isoluminol, pyrogallol, luciferin, naphthalene-1,2-dicarboxylic acid hydrazide derivatives, fluorescein, rhodamine, anthracene, fluorescamine, and ruthenium complexes.

5. The conjugate of claim 1, wherein said polyoxoanion of sulfur or phosphorus is selected from the group consisting of sulfate, sulfonate, sulfinate, phosphate and phosphonate.

6. The conjugate of claim 1, wherein said polyoxoanion of sulfur or phosphorus is sulfonate.

7. The conjugate of claim 1, wherein said oligopeptide has substantially the same amino acid residues and molecular weight as insulin A-chain, said amino acid residues containing a polyoxoanion of sulfur or phosphorus are S-sulfonate-Cys, said amino acid residues linked to said labels are Glu or Asp and the $CO_2H$-terminal amino acid residue, and said ligand is linked to the $H_2N$-terminal amino acid residue.

8. The conjugate of claim 1, wherein said oligopeptide has the same amino acid sequence as insulin A-chain.

9. The conjugate of claim 1, which has the formula:

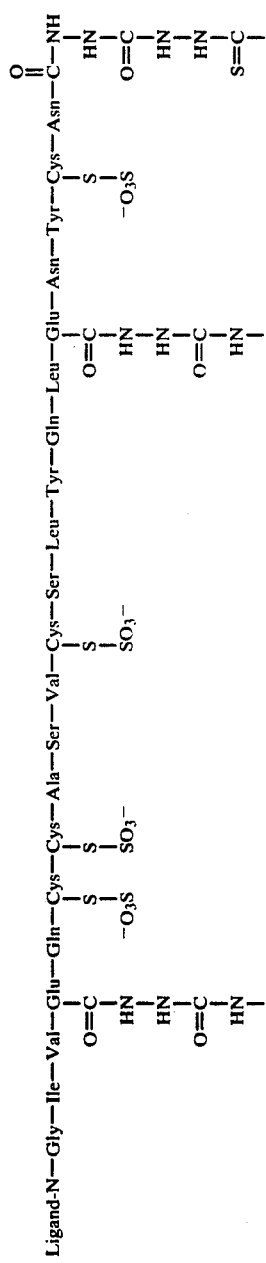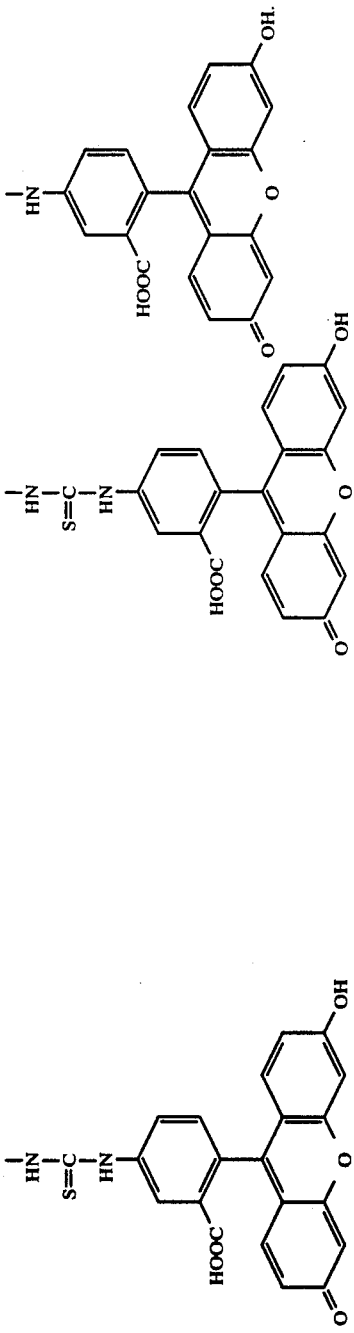

10. The conjugate of claim 1, wherein said ligand or receptor is bonded to said oligopeptide via a spacer group.

11. The conjugate of claim 10, wherein said spacer group contains a thioether group, a disulfide group, or a thiosuccinimidyl group.

12. A ligand compound which is an oligopeptide of 5 to 100 amino acid residues which is bonded to a ligand or receptor, wherein at least one of said amino acid residues contains a polyoxoanion of phosphorus or sulfur and a plurality of said amino acid residues contain a functional group for bonding a chemiluminescent or fluorescent label, wherein said liquid or receptor is selected from the group consisting of drugs, vitamins, antibodies, specific binding proteins, and cell surface receptors.

13. The ligand compound of claim 12, wherein the number of amino acid residues in said oligopeptide is from 10 to 50.

14. The ligand compound of claim 12, wherein the number of amino acid residues in said oligopeptide is from 15 to 25.

15. The ligand compound of claim 12, wherein said polyoxoanion of sulfur or phosphorus is selected from the group consisting of sulfate, sulfonate, sulfinate, phosphate and phosphonate.

16. The ligand compound of claim 12, wherein said polyoxoanion of sulfur or phosphorus is sulfonate.

17. The ligand compound of claim 12, wherein said oligopeptide has substantially the same amino acid residues and molecular weight as insulin A-chain, said amino acid residues containing a polyoxoanion of sulfur or phosphorus are S-sulfonate-Cys, said amino acid residues linked to said labels are Glu or Asp and the CO$_2$H-terminal residue, and said ligand is linked to said H$_2$N-terminal amino acid residue.

18. The ligand compound of claim 12, wherein said oligopeptide has the same amino acid sequence as insulin A-chain.

19. The ligand compound of claim 12, which has the formula:

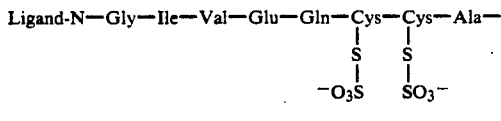

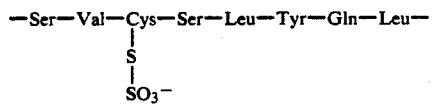

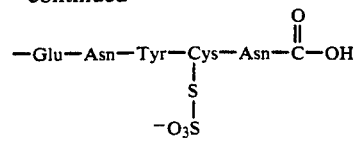

20. The ligand compound of claim 12, wherein said functional group for bonding a chemiluminescent or fluorescent label is —NH$_2$ or —CO$_2$H.

21. The ligand compound of claim 12, wherein said ligand or receptor is bonded to said oligopeptide via a spacer group.

22. The ligand compound of claim 21, wherein said spacer group contains a thioether group, a disulfide group, or a thiosuccinimidyl group.

23. A labeled compound which is an oligopeptide of 5 to 100 amino acid residues in which at least one of said amino acid residues contains a polyoxoanion and a plurality of said amino acid residues are bonded to a chemiluminescent or fluorescent label and one of said amino acid residues contains a unique functional group for bonding a ligand or receptor.

24. The labeled compound of claim 23, wherein the number of amino acid residues in said oligopeptide is from 10 to 50.

25. The labeled compound of claim 23, wherein the number of amino acid residues in said oligopeptide is from 15 to 25.

26. The labeled compound of claim 23, wherein said chemiluminescent label is selected from the group consisting of luminol, isoluminol, pyrogallol, luciferin, naphthalene-1,2-dicarboxylic acid hydrazide derivatives, fluorescein, rhodamine, anthracene, fluorescamine, and ruthenium complexes.

27. The labeled compound of claim 23, wherein said polyoxoanion of sulfur or phosphorus is selected from the group consisting of sulfate, sulfonate, sulfinate, phosphate and phosphonate.

28. The labeled compound of claim 23, wherein said polyoxoanion of sulfur or phosphorus is sulfonate.

29. The labeled compound of claim 23, wherein said unique functional group for bonding a ligand or receptor is —NH$_2$ or —CO$_2$H.

30. The labeled compound of claim 23, wherein said oligopeptide has substantially the same amino acid residues and molecular weight as insulin A-chain, said amino acid residues containing a polyoxoanion of sulfur or phosphorus are S-sulfonate-Cys, said amino acid residues linked to said labels are Glu or Asp and the CO$_2$H-terminal residue, and said ligand is linked to the H$_2$N-terminal amino acid residue.

31. The labeled compound of claim 23, wherein said oligopeptide has the same amino acid sequence as insulin A-chain.

32. The labeled compound of claim 23, which has the formula:

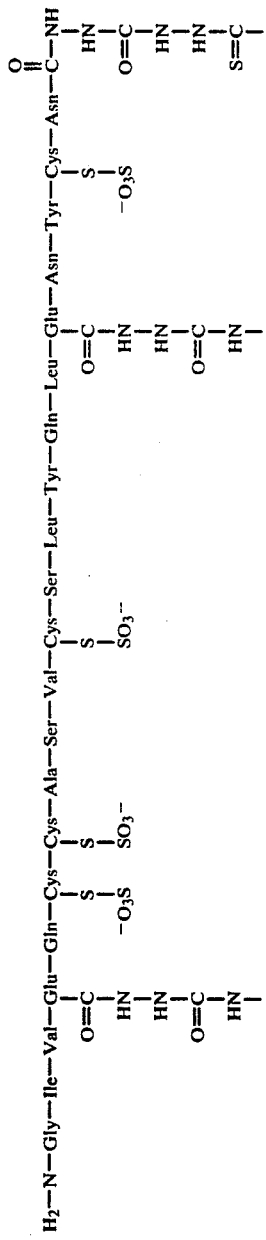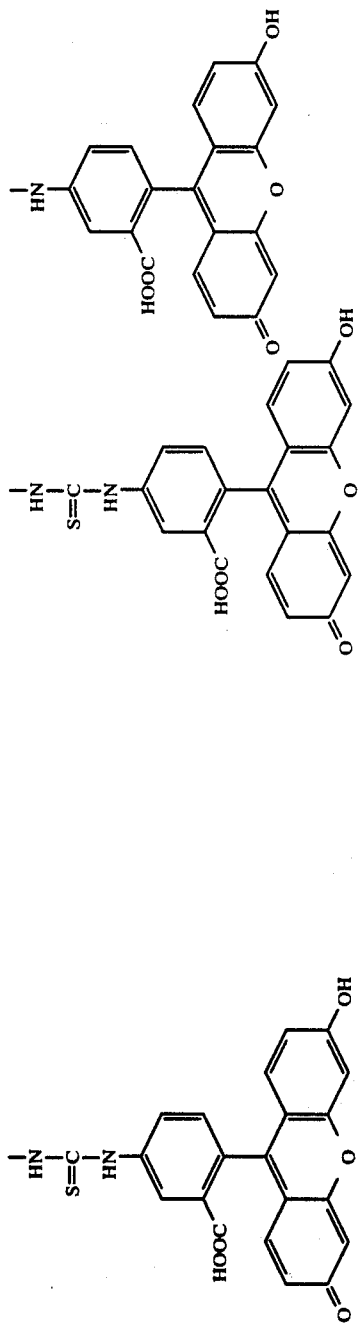

33. A kit, comprising (i) a ligand-label conjugate, which is an oligopeptide of 5 to 100 amino acid residues, which is bonded to a ligand or a receptor, wherein at least one of said amino acid residues contains a polyoxoanion of sulfur or phosphorus and a plurality of said amino acid residues are linked to a chemiluminescent or fluorescent label, and (ii) a binding complement of said ligand or receptor.

34. The kit of claim 33, wherein the number of amino acid residues in said oligopeptide is from 10 to 50.

35. The kit of claim 33, wherein the number of amino acid residues in said oligopeptide is from 15 to 25.

36. The kit of claim 33, wherein said chemiluminescent label is selected from the group consisting of luminol, isoluminol, pyrogallol, luciferin, naphthalene-1,2-dicarboxylic acid hydrazide derivatives, fluorescein, rhodamine, anthracene, fluorescamine, and ruthenium complexes.

37. The kit of claim 33, wherein said polyoxoanion of sulfur or phosphorus is selected from the group consisting of sulfate, sulfonate, sulfinate, phosphate and phosphonate.

38. The kit of claim 33, wherein said polyoxoanion of sulfur or phosphorus is sulfonate.

39. The kit of claim 33, wherein said oligopeptide has substantially the same amino acid residues and molecular weight as insulin A-chain, said amino acid residues containing a polyoxoanion of sulfur or phosphorus are S-sulfonate-Cys, said amino acid residues linked to the labels are Glu or Asp and the $CO_2H$-terminal residue, and said ligand is linked to the $H_2N$-terminal amino acid residue.

40. The kit of claim 33, wherein said oligopeptide has the same amino acid sequence as insulin A-chain.

41. The kit of claim 33, wherein said ligand-label conjugate has the formula:

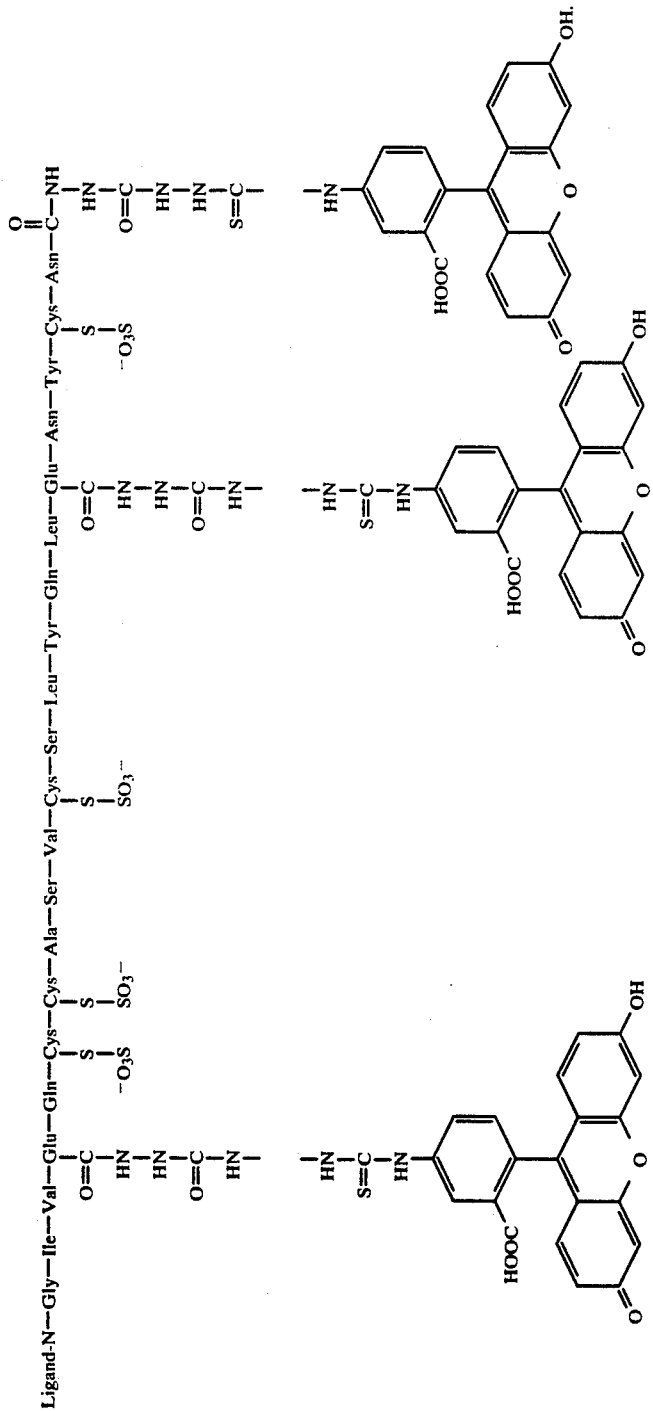

42. The kit of claim 33, further comprising a sample of said ligand or receptor.

43. The kit of claim 42, wherein said sample of said ligand or receptor contains a known amount of said ligand or receptor.

44. The kit of claim 33, wherein said binding complement of said ligand or receptor is present in the form of a sample of a known amount.

45. The kit of claim 33, wherein said ligand or receptor is bonded to said oligopeptide via a spacer group.

46. The kit of claim 45, wherein said spacer group contains a thioether group, a disulfide group, or a thiosuccinimidyl group.

* * * * *